(12) United States Patent
Gornushkin et al.

(10) Patent No.: US 7,161,672 B2
(45) Date of Patent: Jan. 9, 2007

(54) MATERIAL IDENTIFICATION EMPLOYING A GRATING SPECTROMETER

(75) Inventors: Ignor B. Gornushkin, Gainesville, FL (US); James D. Winefordner, Gainesville, FL (US); Benjamin W. Smith, Gainesville, FL (US)

(73) Assignee: University of Florida Research Foundation, Incorporated, Gainsville, FL (US)

( * ) Notice: Subject to any disclaimer, the term of this patent is extended or adjusted under 35 U.S.C. 154(b) by 0 days.

(21) Appl. No.: 10/798,838

(22) Filed: Mar. 12, 2004

(65) Prior Publication Data

US 2005/0002029 A1 Jan. 6, 2005

Related U.S. Application Data

(60) Provisional application No. 60/453,968, filed on Mar. 13, 2003.

(51) Int. Cl.
*G01J 3/28* (2006.01)

(52) U.S. Cl. .................... 356/328; 356/326
(58) Field of Classification Search ........... 356/328, 356/326
See application file for complete search history.

(56) References Cited

U.S. PATENT DOCUMENTS

| | | | |
|---|---|---|---|
| 5,508,525 A * | 4/1996 | Day et al. ............ | 250/339.07 |
| 5,568,251 A | 10/1996 | Davies et al. | |
| 5,885,531 A * | 3/1999 | Heffelfinger et al. .... | 422/82.08 |
| 6,339,662 B1 | 1/2002 | Koteles et al. | |
| 6,538,737 B1 | 3/2003 | Sandstrom et al. | |
| 6,539,149 B1 | 3/2003 | Barbarossa et al. | |
| 6,569,685 B1 * | 5/2003 | Carlson et al. ............ | 436/172 |
| 6,573,989 B1 | 6/2003 | Suzuki et al. | |
| 2002/0101587 A1 * | 8/2002 | Wilson et al. .............. | 356/328 |
| 2003/0223059 A1 * | 12/2003 | Li ............................... | 356/317 |
| 2004/0001201 A1 * | 1/2004 | Knapp ........................ | 356/326 |

OTHER PUBLICATIONS

I. B. Gornushkin et al. "Identification Of Solid Materials by Correlation Analysis Using a Microscopic Laser-Induced Plasma Spectrometer" Analytical Chemistry, vol. 71, No. 22, pp. 5157-5164, Nov. 15, 1999.

Gornushkin et al., "Identification of Solid Materials by Correlation Analysis Using a Microscopic Laser-Induced Plasma Spectrometer", Analytic Chemistry, vol. 71, No. 22, pp. 5157-5164, Nov. 15, 1999.

* cited by examiner

*Primary Examiner*—Gregory J. Toatley, Jr.
*Assistant Examiner*—Kara Geisel
(74) *Attorney, Agent, or Firm*—Miles & Stockbridge PC; Dennis P. Clarke

(57) ABSTRACT

Multi-ordered spectral data is obtained from various known substances and is stored in a spectral library. The identification of an unknown material is accomplished by correlating the sample's multi-ordered spectrum against all or a portion of the spectrum in the library, and finding the closest match.

21 Claims, 5 Drawing Sheets

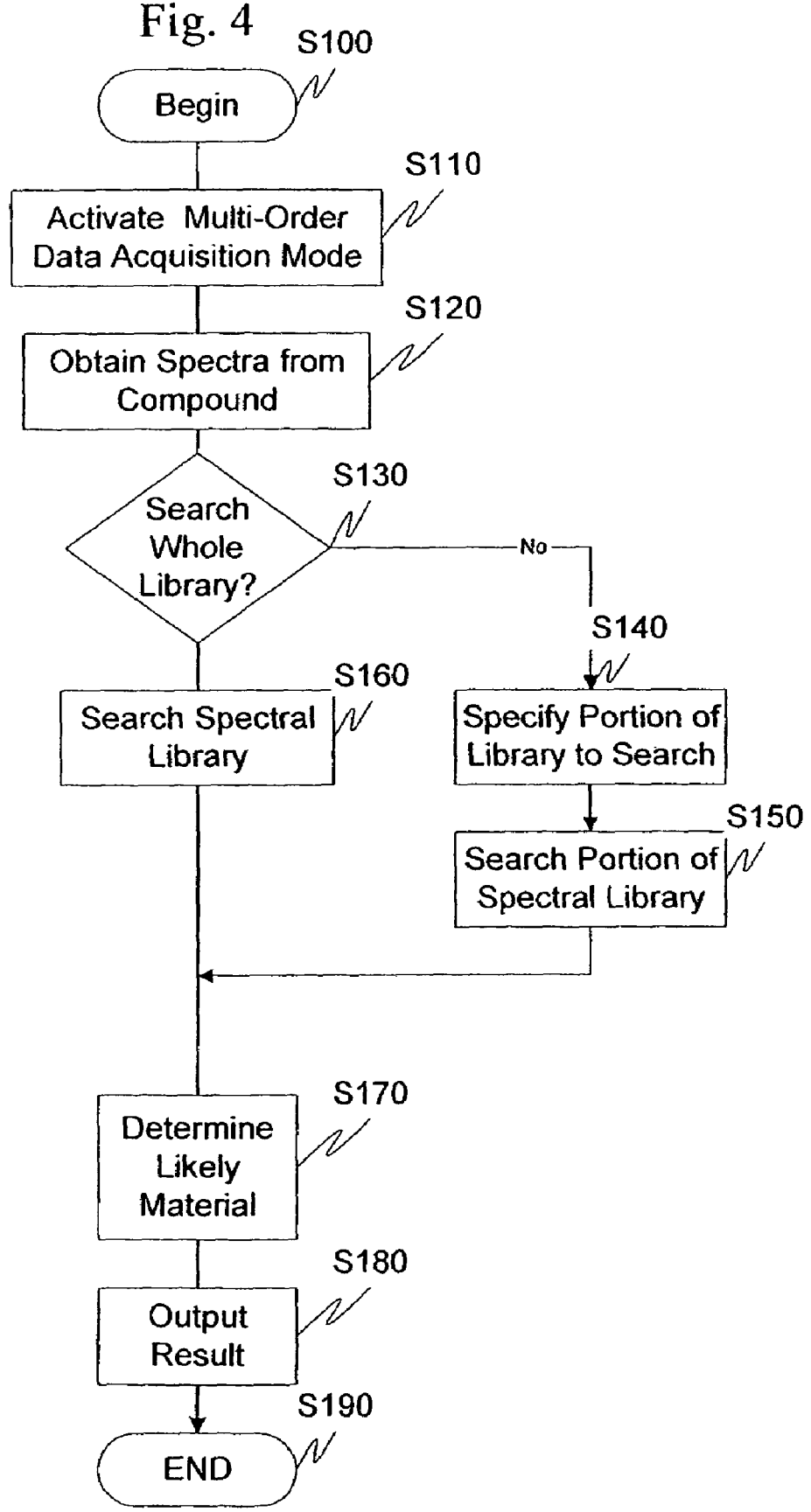

MATERIAL IDENTIFICATION EMPLOYING A GRATING SPECTROMETER

RELATED APPLICATION DATA

This application claims the benefit of and priority under 35 U.S.C. §119(e) to U.S. patent application Ser. No. 60/453,968, filed Mar. 13, 2003, entitled "Method of Material Identification Employing Grating Spectrometer" which is incorporated herein by reference in its entirety.

GOVERNMENT INTERESTS

This study was support by the U.S. Department of Energy, Contract No. DEFG02-99ER 14960.

BACKGROUND

1. Field of the Invention

The invention generally relates to methods and systems for the identification of unknown materials employing spectral information associated with the material.

2. Description of Related Art

The reliable identification of unknown materials relies upon the amount of information that can be obtained from measurements of physical or chemical characteristics of the material. One such identification methodology uses spectral information. Each material is characterized by its own unique spectral fingerprint. The spectral fingerprint may comprise absorption, emission, Raman or any other type of spectral data obtained with the use of a characterization technique.

Grating spectrometers are conventionally employed to identify unknown materials and usually include a grating arrangement with a diffraction grating, which has a plurality of grating grooves extending closely side by side. An incident light beam enters through an entrance slit, is collimated and is directed on the grating by a suitable optical system. The light returned by a diffraction grating is spectrally dispersed. Light of different wavelengths is separated by angles for which the optical wavelength difference of the light diffracted at the grating grooves amounts to an integral multiple of the wavelength. The light of each wavelength is thus returned at different angles corresponding to optical wavelength differences of integer, i.e., one, two, three etc., wavelength multiples. An incident white parallel light beam is therefore dispersed into parallel light beams of different colors, i.e., corresponding to different wavelengths, and returned at different angles. Several of such light beams, which correspond to path length differences of the single, double, triple, etc., of the wavelength, are thereby associated with each wavelength. These different diffracted light beams of a wavelength are generally called "grating orders." Light at a particular wavelength $\lambda$ in the first grating order is diffracted by a grating in a particular direction. Light at a wavelength $\lambda/2$, $\lambda/3$, $\lambda/4$ . . . is also diffracted in the same direction as for light at the wavelength $\lambda$. These added components are said to be in the second, third, fourth . . . grating order.

The diffracted light beams are focused by an optical system, such that, in the plane of an exit slit, a spectrum is generated which is composed of real images of the entrance slit generated by the light beams of different colors. The exit slit permits passage of light therethrough, which light has been diffracted in a certain direction and which is focused by the optical system at the location of the exit slit. The light emerging through the exit slit is directed to a detector. By rotating the diffraction grating the spectrum is scanned. That is, the light beams diffracted into the different directions can be directed consecutively to the exit slit.

Spectrometers without an exit slit in which the diffracted light beams are focused by the optical system onto a diode array are also known. In this type of spectrometer, a plurality of photodiodes are arranged closely side by side. When such a diode array is used the spectrum is not scanned, but the different wavelengths are simultaneously detected and the associated detector signals are output in parallel.

In conventional grating spectrometry, however, it is desired to measure only light of one grating order. Usually only the first grating order is used. The undesired grating orders thus, in typical operations, must be suppressed. This is usually achieved by a cut-off filter or by a prism pre-monochomator. In the UV range, air is effective as a suitable cut-off filter.

In the first grating order, a filter may be used for the spectral range of about 100 nm before a higher grating order occurs and the filter must be changed. A single diffraction grating, however, may sweep the spectral range from 190 nm to 900 nm. This large spectral range requires a correspondingly large number of filters, each of which must be consecutively rotated into the path of rays. Each filter change varies the optical conditions, such that filter steps or filter spikes easily occur in the 100%, or first order-line.

Another exemplary disadvantage of a diffraction grating, which is used in the first grating order through a large wavelength range, is the low efficiency of the diffraction grating near the ends of the range. This reduction of the efficiency often coincides with a decrease of the spectral lamp intensity or of the spectral detector sensitivity.

It is known to use the diffraction grating in a relatively long wave partial range in the first grating order, and in a relatively short wave partial range in a second grating order. This requires, however, a more frequent filter change and the use of band pass filters.

When a diode array is used as a detector, a quite narrow spectral range—a few tens of nm, at best, is detected thereby, and the higher grating orders must be suppressed by a cut-off filter. As the slopes of the cut-off filter are not infinitely steep, the range, which may be detected by the diode array at once, is even smaller. In order to measure a larger spectral range with such a detector arrangement, it is necessary to record the spectrum section by section and to rotate the diffraction grating therebetween.

SUMMARY

An exemplary aspect of this invention relates to using multi-order spectra for material identification.

Another exemplary aspect of the invention relates to providing an improved system for the identification of unknown materials utilizing grating spectrometers that is not subject to the disadvantages associated with conventional grating spectrometers.

The exemplary system and methodology is based upon the obtention of spectral data from various substances and storing them in the form of a spectral library. Identification of an unknown material is accomplished by correlating its spectrum against all spectra in the library and finding the closest match.

The proposed technical solution allows one to obtain a larger amount of spectroscopic information than in conventional spectroscopy without or with only a minor modification of existing grating spectral instruments. Grating spectrometers are designed in such a way that only one order of diffraction (usually the first order) is used to obtain easily identifiable spectra in the focal plane of the spectrometer. If two or more orders are displayed simultaneously, the deciphering of the spectrum becomes problematic. For example, if the grating is set at 600 nm, the spectrometer will display a wavelength of 600 nm in the first order, 300 nm in the second order, and 200 nm in the third order. Sometimes, suppression of higher orders is built into the design of the spectrometer. Order-sorting filters are also sometimes used to correct this inherent problem.

Thus, in conventional spectroscopy, order overlap is considered undesirable. However, in the identification methodology and system of the present invention, based on correlation analysis, such overlap is beneficial because there is no need to assign spectral features. The spectrum is used as a fixed piece of information without detailing its content. Multiple order spectra provide more simultaneous useful information for the correlation process. Of course, this occurs at the expense of a partial loss in the spectral resolution (if lines from different orders overlap), but this effect is overshadowed by the inherent benefits for correlation analysis and its application to reliable material identification.

In general, the invention invokes the use of multiple or all possible diffraction orders available in spectrometers, such as grating spectrometers, for material identification based on correlation analysis. The technical solution (the use of the multi-order data acquisition mode) functions in combination with the correlation software of the invention. Technically, many grating spectrometers already have the built-in capability to monitor more than one diffraction order. This capability is inherent in the grating spectrometers design. For those spectrometers which lack this capability, only a slight modification is necessary to restore the capability to monitor more than one diffraction order.

The exemplary methodology and system of the invention may also be employed successfully utilizing Echelle grating spectrometers. The Echelle spectrometer is designed to work in a multi-order regime. A cross dispersion element (a prism) is used in Echelle spectrometers as an order sorter. However, no cross dispersion element is required for the reliable correlation analysis achievable with the system of the invention. Thus, cheap and simple Echelle grating spectrometers may be employed for material identification.

BRIEF DESCRIPTION OF THE DRAWINGS

FIG. 4 illustrates an exemplary method of multi-order spectroscopy according to this invention.

DETAILED DESCRIPTION

The exemplary systems and methods of this invention will be described in relation to a spectroscopy system and methodology. However, to avoid unnecessarily obscuring the present invention, the following description omits well-known structures and devices that may be shown in block diagram form or otherwise summarized. For the purpose of explanation, numerous specific details are set forth in order to provide a thorough understanding of the present invention. It should be appreciated, however, that the present invention may be practiced in a variety of ways beyond the specific details set forth herein. For example, any type of spectroscopic technique and equipment can be used to obtain the spectral data as discussed herein.

Furthermore, while the exemplary embodiments illustrated herein show the various components of the spectroscopy system collocated, it is to be appreciated that the various components of the system can be located at distant portions of a distributed network, such as a telecommunications network and/or the Internet, a distributed network, or within a dedicated spectroscopy system. Thus, it should be appreciated that the various components illustrated herein can be combined into one or more devices or collocated on a particular node of a distributed network, such as a telecommunications network, the Internet, a private network, a secured or unsecured network or any combination thereof. It will be appreciated from the following description, and for reasons of computational efficiency, that the components of the spectroscopy system can be arranged at any location within a distributed network without affecting the operation of the system.

Furthermore, it should be appreciated that the various links connecting the elements can be wired or wireless links, or any combination thereof, or any other known or later developed element(s) that is capable of supplying and/or communicating information to and from the connected elements. Additionally, the term module as used herein can refer to any known or later developed hardware, software or combination of hardware and software that is capable of performing the functionality associated with that element.

Figure 1:
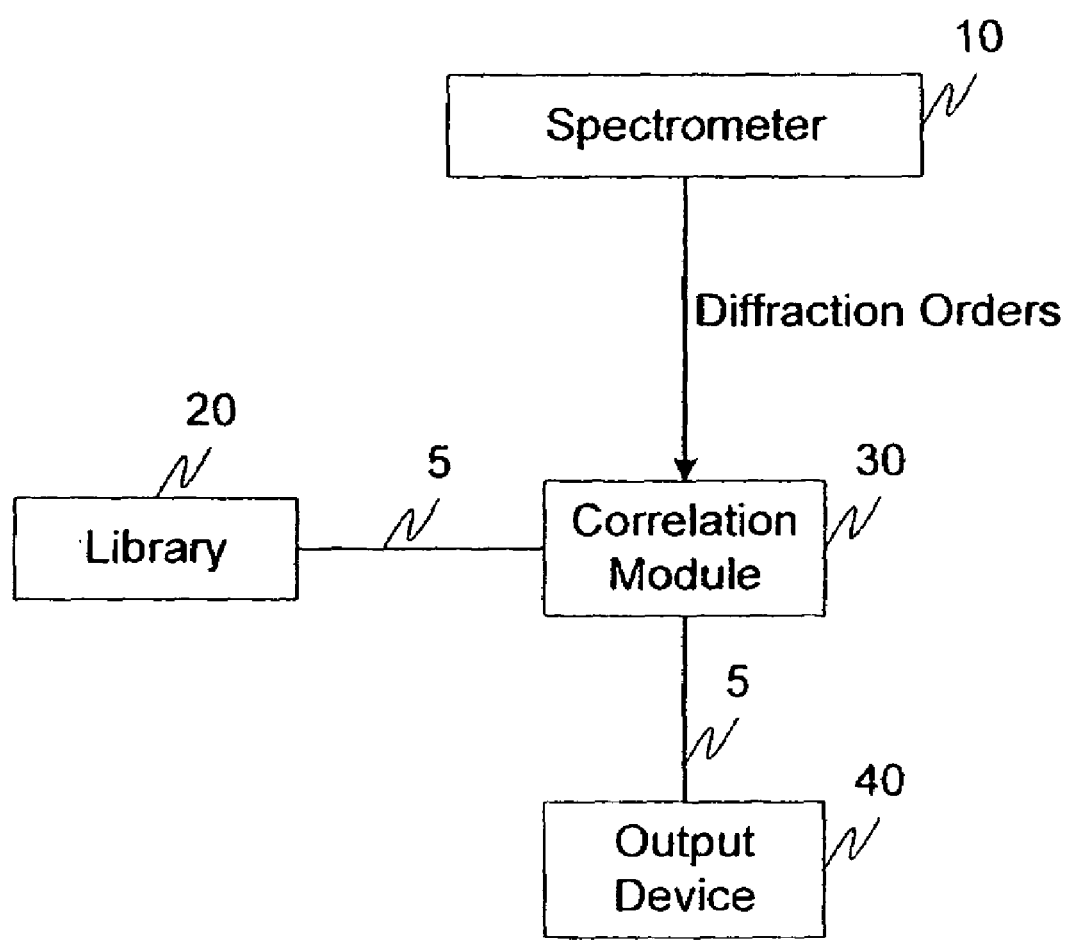
FIG. 1 illustrates a block diagram of an exemplary multi-order spectroscopy system according to this invention.

FIG. 1 illustrates and exemplary spectroscopy system according to this invention. The spectroscopy system includes a spectrometer 10, a correlation module 30, such as a computer, one or more libraries 20 and an output device 40, all interconnected via links 5. The spectrometer 10 can be any type of spectrometer that is capable of outputting multi-order spectral data. Alternatively, the correlation module 30 can process single-order spectral data from the spectrometer 10 and assemble a plurality of spectra to create multi-ordered spectra. This can be achieved in software by combining spectra from a few spectral windows centered at integer multiples of a certain wavelength. The output device 10 can be any output device, such as, but not limited to, a personal computer, a display, an electronic messaging device, or the like.

In operation, spectral data is received from the spectrometer 10, and in accordance with an exemplary embodiment of this invention, two or more spectra are forwarded to the correlation module 30. The correlation module 30, in cooperation with the library 20, performs a correlation, such as the linear and rank correlation described in the article "Identification of Solid Materials By Correlation Analysis Using A Microscopic Laser-Induced Plasma Spectrometer," Analytical Chemistry, Vol. 71, No. 22, Nov. 15, 1999, which is incorporated herein by reference.

However, it should be appreciated that any type of correlation technique can be used to compare the multi-order spectra with the spectra contained in library 20.

The library 20 comprises a plurality of spectral fingerprints based on multi-order spectral information. The library can be categorized into, for example, various categories based on, for example, the number of spectra analyzed, or any other categorical classification. For example, in order to speed searching during the correlation process, a user could specify one or more categories or subcategories of information in the library 20 based on, for example, the number of analyzed spectra or the general composition of the material, such as a metal, or the like.

Figure 2:
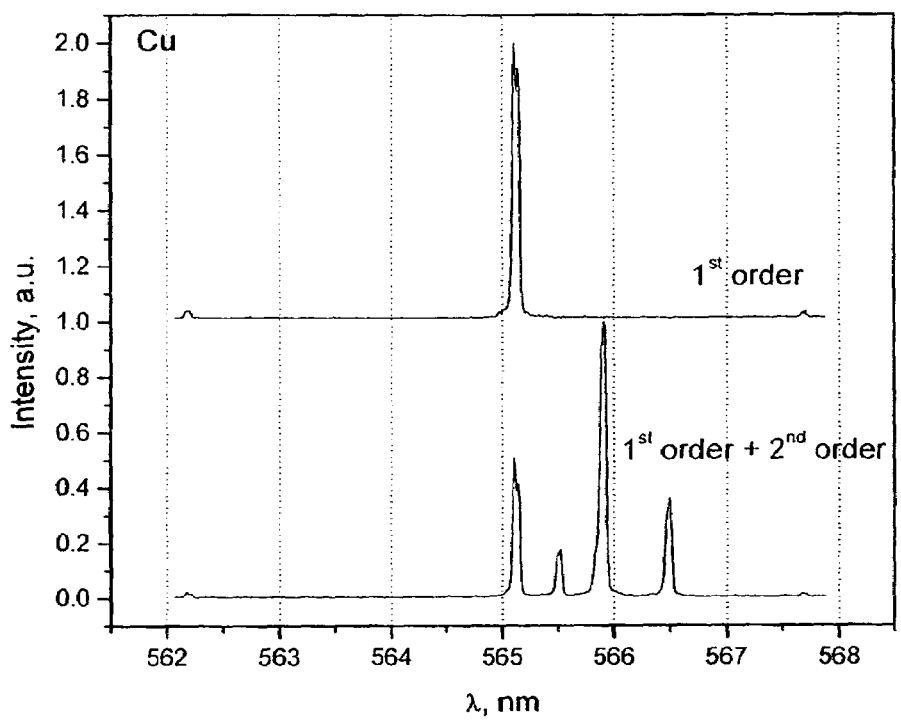
FIG. 2 illustrates a comparison of two spectra according to this invention.
Figure 3:
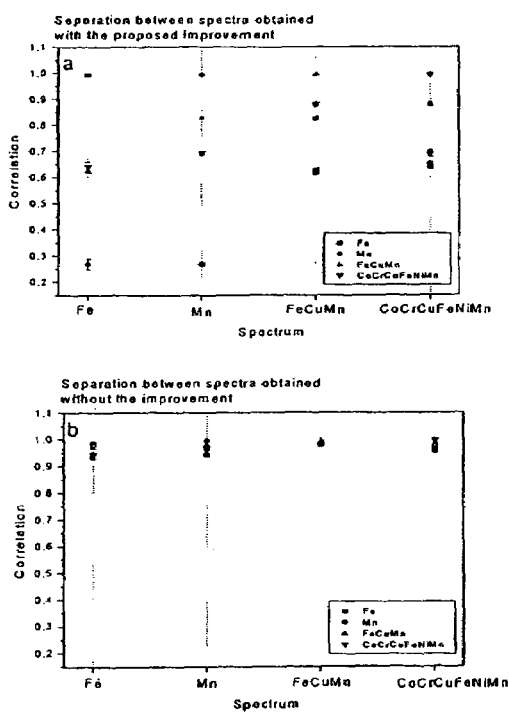
FIG. 3 illustrates a comparison of the correlation of the two spectra illustrated in FIG. 2 according to this invention.
Figure 6:
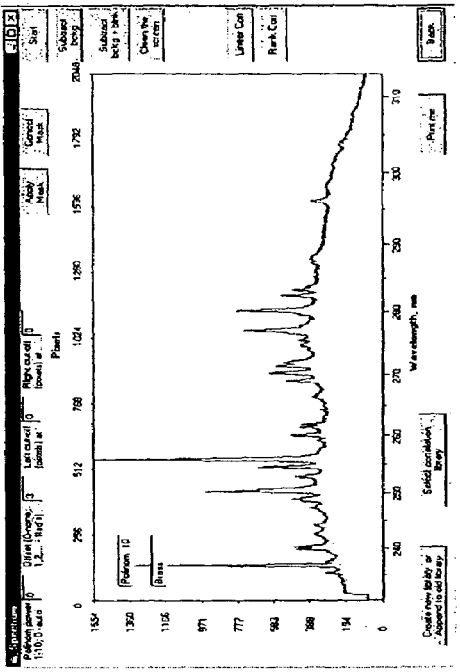
FIGS. 5–8 illustrate exemplary user interfaces associated with the methodology outlined in FIG. 4.
Figure 5:
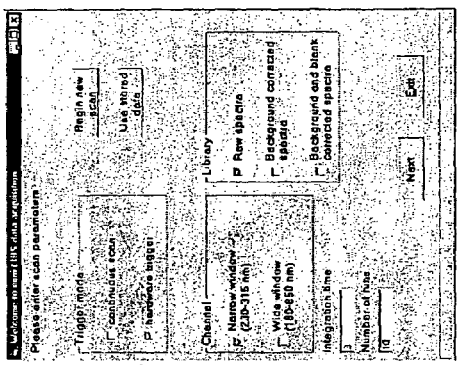

FIG. 2 illustrates two exemplary spectra for copper wherein the upper spectrum is obtained in a first order and a second spectrum is a combination of first and second orders. The combined order spectrum carries four-fold as much spectral information as compared to the first spectra. Another example is given in FIG. 3 which illustrates the improvement upon the application of the proposed methodology for identification of spectra from light sources containing pure transient metals or their combinations (pure Fe and pure Mn, or the combinations Fe+Cu+Mn and Fe+Cu+Mn+Co+Cr+Ni). As one can see from FIG. 3, window b, with the use of only the first diffraction order, spectra correlate with each other very well (close points on the graph) and, therefore, they are practically inseparable. This means that one can barely see the difference between all four light sources. The situation is completely different with the use of the multiple order (two orders) spectra (FIG. 3, window a). Here, the correlation is poor between the spectra other than the correct one, thus resulting in a large separation of the points on the graph and, therefore, in a reliable spectra identification.

More particularly, FIG. 3 illustrates how the correlation module 30 identifies the spectra. The exemplary correlation module 30 utilizes software based on a strict statistical correlation methodology, however other correlation techniques could be used such as, but not limited to principal component analysis, partial least squares, genetic regression algorithms, and the like.

FIG. 4 illustrates an exemplary method for performing multi-order spectral analysis according to this invention. In particular, control begins at step S100 and continues to step S110. In step S110, the multi-order data acquisition mode is selected, if needed. Next, in step S120, the spectra are obtained from the compound under test. Optionally, as discussed above, a plurality of single spectrum can be assembled to produce a multi-order spectra. Then, in step S130, a determination is made whether to search all or a portion of the "spectral library." For example, a user can be queried as to which portion(s) of the library are to be searched.

The spectral library could be the entirety of spectral information available in a plurality of libraries worldwide, or for example, spectral libraries for specific materials can be stored at geographically diverse locations and may, for example, be further sub-divided into material type categories. In general, the user can have available for the search all possible spectral information or a portion thereof.

If the entire spectral library is to be searched, control continues to step S160 where the obtained spectra is compared with the spectra stored in the spectra library through, for example, a statistical correlation. Control then continues to step S170.

If only a portion of a spectral library is to be searched, control continues to step S140 where a portion of a spectral library is specified and then in step S150, the obtained spectra are compared with the spectra stored in the selected portion of the spectra library. Control then continues to step S170.

In step 170, the identification of the material is achieved. Next, in step S180, the result of the identification is output and control continues to step S190 where the control sequence ends.

FIGS. 5–8 illustrate various user interfaces that can be associated with the methodology discussed above in relation to FIG. 4. In particular, FIG. 5 allows a user to select various scanning parameters, such as a trigger mode, the channel and library. Upon selecting the scanning parameters, the multi-order data is acquired and displayed in the user interface illustrated in FIG. 6. From this user interface, users can select various features directed toward how to handle the acquired spectrum, such as to create a new library or append the acquired spectrum to an old library, to select a correlation library, to print the spectrum, masking options, background options, the correlation technique, printing, or the like.

Figure 7:
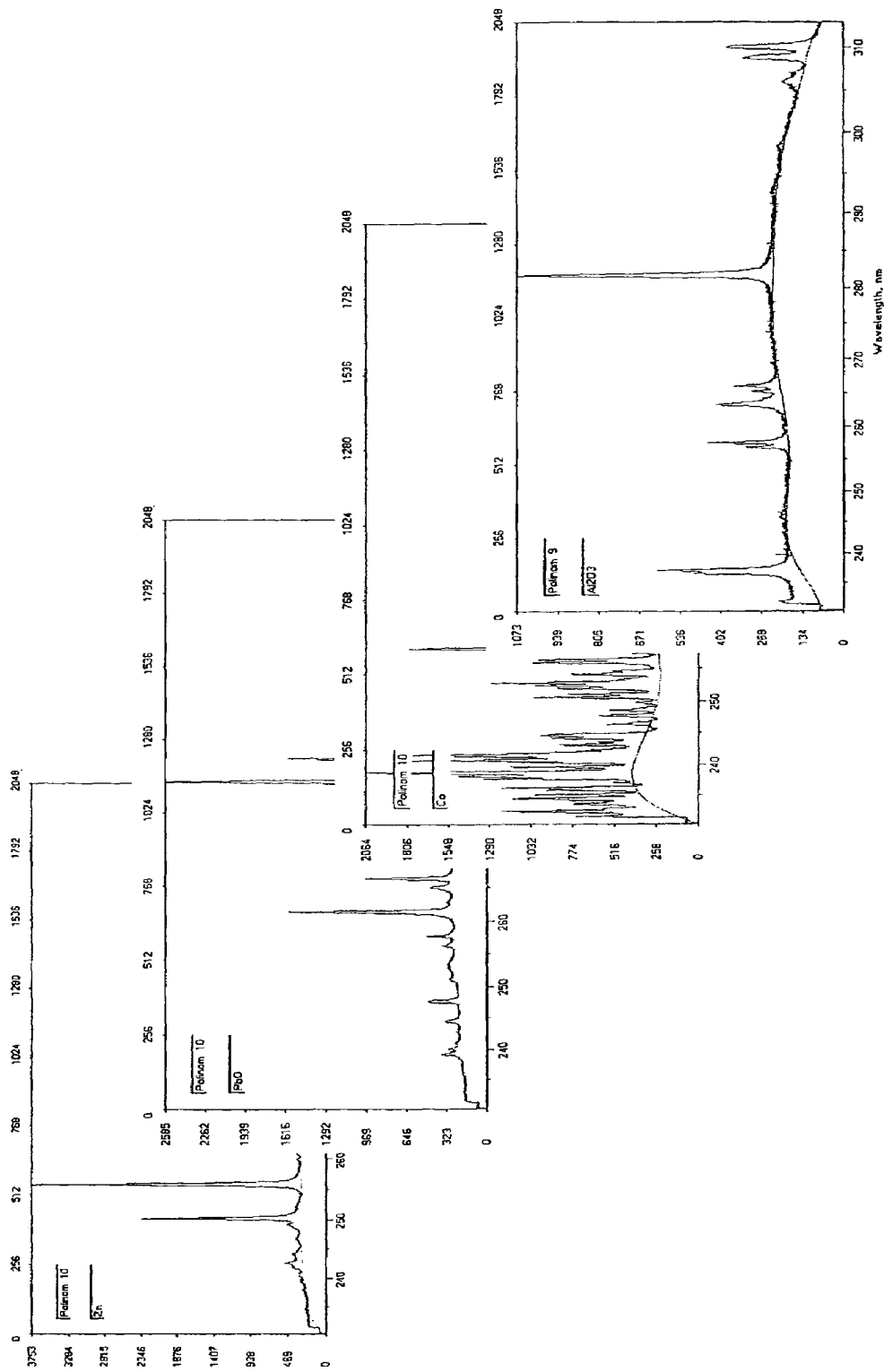

FIG. 7 illustrates various spectra that are stored in the library 20 and are used by the correlation module 30 for the comparison between the acquired sample spectrum and spectral information specific to known compounds.

Figure 8:
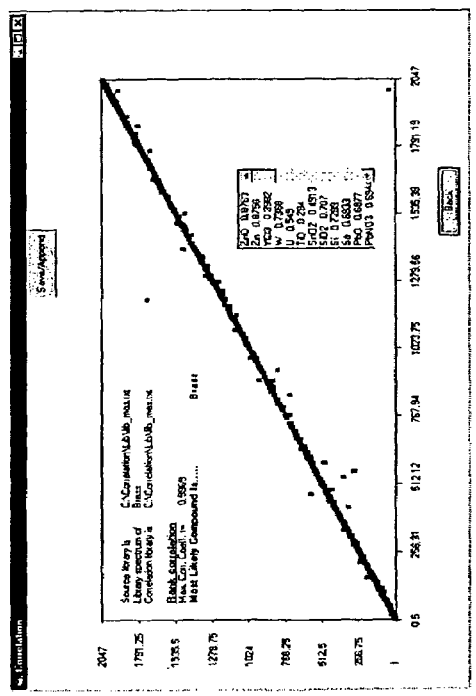

FIG. 8 illustrates a user interface summarizing the most likely compound identification. This interface can include, but is not limited to, the source library, library spectrum information, correlation library information and a correlation coefficient, such as the maximum correlation coefficient. Furthermore, and not illustrated, the system can also display one or more next most likely compound identifications.

An exemplary embodiment was designed as an interface for multi-array optic detectors (such, for example, the detectors from the Ocean Optics, Inc.(USA), containing 2,000–14,000 sensitive elements), and the correlation module used simple linear and rank correlation. This relationship provided an extremely effective approach to detecting minute differences in spectra of various materials.

The multi-order data acquisition mode combined with the correlation software can be applied to a large variety of materials with the aim being their ultimate identification. For obtaining spectral data, any sort of spectroscopic technique can be used. As discussed above, these include, but are not limited to, inductively-coupled plasma (ICP), laser-induced breakdown spectroscopy (LIBS), flame spectroscopy, or the like. The proposed methodology can be used immediately with many grating spectrometers which do not have a built-in order sorter. Those having such a sorter can be quickly modified to restore multi-order capability.

In practice and with the use of the proposed methodology, minute differences in materials can be detected, for example, in real time or near real time. The methodology can be used to sort recycled plastics, minerals, differing types of steel, alloys, or the like. It also can also be directed to the reliable identification of biological materials including, but not limited to, threatening biological agents and the like.

Use of the multi-order data collection system and methodology combined with the correlation software of the invention will be beneficial for the mining, material processing or recycling industries. It can substantially improve spectral methods aimed at rapid material identification. In the mining industry, for example, it can help to quickly identify beneficiary layers from overburden. In recycling, it can quickly sort recyclable materials (different sorts of plastics or metals, for example). Coupled with LIBS or Raman spectrometers, the methodology reduces sample preparation and helps to avoid time and material-consuming chemical analysis.

The above-described system can be implemented on a computing device, such as a personal computer, dedicated spectral analysis system, or the like, or a separate programmed general purpose computer having spectral scanning capabilities. Additionally, the systems and methods of this invention can be implemented on a special purpose computer, a programmed microprocessor or microcontroller and peripheral integrated circuit element(s), and ASIC or other integrated circuit, a digital signal processor, a hard-wired electronic or logic circuit such as a discrete element circuit, a programmable logic device such as a PLD, PLA, FPGA, PAL, or the like. In general, any device capable of implementing a state machine that is in turn capable of implementing the processes described herein can be used to implement the multi-order spectrum analysis system according to this invention.

Furthermore, the disclosed methods may be readily implemented in software using object or object-oriented software development environments that provide portable source code that can be used on a variety of computer or workstation platforms. Alternatively, the disclosed system may be implemented partially or fully in hardware using standard logic circuits or, for example, a VLSI design. Whether software or hardware is used to implement the systems in accordance with this invention is dependent on the speed and/or efficiency requirements of the system, the particular function, and the particular software or hardware systems or microprocessor or microcomputer systems being utilized. The systems and methods illustrated herein can be readily implemented in hardware and/or software using any suitable systems or structures, devices and/or software, such as JAVA®, by those of ordinary skill in the applicable art from the functional description provided herein and with a basic general knowledge of the computer and spectrum acquisition arts.

Moreover, the disclosed methods may be readily implemented in software executed on a programmed general purpose computer, a special purpose computer, a microprocessor, or the like. In these instances, the systems and methods of this invention can be implemented as a program embedded on a personal computer such as a JAVA®, CGI or Perl script, as a resource resigning on a server or graphics workstation, as a routine embedded in a dedicated spectral analysis system, or the like. The systems and methods of this invention can also be implemented by physically incorporating this system and method into a software and/or hardware system, such as the hardware and software systems of a computer.

The invention claimed is:

1. A method for identifying an unknown material comprising:
    obtaining a multi-order spectrum from a sample of said unknown material, wherein the multi-order spectrum comprises a plurality of simultaneously obtained diffraction orders;
    comparing the obtained multi-order spectrum to multi-order spectra for known materials; and
    outputting an identification of the sample based on a correlation between the multi-order spectrum from the sample and the multi-order spectra for the known materials.

2. The method of claim 1, further comprising outputting one or more next closest identifications based upon the correlation between the multi-order spectrum from the sample and the multi-order spectra for known compositions.

3. The method of claim 1, wherein the correlation is a linear and a rank correlation.

4. The method of claim 1, wherein the correlation is a statistical correlation.

5. The method of claim 1, further comprising building a library of spectra for the known materials.

6. The method of claim 1, wherein the comparison can be performed against a spectral library or a portion of a spectral library.

7. The method of claim 1, wherein the multi-order sample spectrum comprises at least a first and a second order spectra.

8. The method of claim 1, wherein the multi-order sample spectrum comprises all spectra.

9. The method of claim 1, further comprising outputting a correlation coefficient.

10. The method of claim 1, further comprising displaying a summary of the correlation.

11. A system for identifying an unknown material comprising:
    a spectrometer adapted to obtain a multi-order spectrum from a sample of said unknown material, wherein the multi-order spectrum comprises a plurality of simultaneously obtained diffraction orders;
    a correlation module adapted to compare the obtained multi-order spectrum to multi-order spectra for known materials; and
    an output device adapted to output an identification of the sample based on a correlation between the multi-order spectrum from the sample and the multi-order spectra for the known materials.

12. The system of claim 11, wherein the output device outputs one or more next closest identifications based upon the correlation between the multi-order spectrum from the sample and the multi-order spectra for known materials.

13. The system of claim 11, wherein the correlation is a linear and a rank correlation.

14. The system of claim 11, wherein the correlation is a statistical correlation.

15. The system of claim 11, wherein the output device as adapted to build a library of spectra for the known materials.

16. The system of claim 11, wherein the comparison can be performed against a spectral library or a portion of a spectral library.

17. The system of claim 11, wherein the multi-order sample spectrum comprises at least a first and a second order spectra.

18. The system of claim 11, wherein the multi-order sample spectrum comprises all spectra.

19. The system of claim 11, wherein the output device determines and outputs a correlation coefficient.

20. The system of claim 11, wherein the output device cooperates with the correlation module to display a summary of the correlation.

21. A system for identifying an unknown material comprising:
    means for obtaining a multi-order spectrum from a sample of said unknown material, wherein the multi-order spectrum comprises a plurality of simultaneously obtained diffraction orders;
    means for comparing the obtained multi-order spectrum to multi-order spectra for known materials; and
    means for outputting an identification of the sample based on a correlation between the multi-order spectrum from the sample and the multi-order spectra for the known materials compositions.

* * * * *

UNITED STATES PATENT AND TRADEMARK OFFICE
CERTIFICATE OF CORRECTION

| | |
|---|---|
| PATENT NO. | : 7,161,672 B2 |
| APPLICATION NO. | : 10/798838 |
| DATED | : January 9, 2007 |
| INVENTOR(S) | : Igor B. Gornushkin, James D. Winefordner and Benjamin W. Smith |

It is certified that error appears in the above-identified patent and that said Letters Patent is hereby corrected as shown below:

On the Title Page at heading (75), please correct the spelling of the first inventor's first name:

Change "Ignor" to --Igor--;

At heading (73) Assignee, please correct the spelling of city of the address of the Assignee:

Change "Gainsville" to --Gainesville--

Signed and Sealed this

First Day of May, 2007

JON W. DUDAS
*Director of the United States Patent and Trademark Office*